United States Patent [19]

Bowers et al.

[11] Patent Number: 5,656,727

[45] Date of Patent: Aug. 12, 1997

[54] ANTAGONISTS OF LHRH

[75] Inventors: Cyril Y. Bowers, New Orleans, La.; Karl A. Folkers, Austin, Tex.; Anna Janecka, Lodz, Poland

[73] Assignees: The Administrators of the Tulane Educational Fund, New Orleans, La.; Board of Regents, The University of Texas System, Austin, Tex.

[21] Appl. No.: 430,602

[22] Filed: Apr. 28, 1995

Related U.S. Application Data

[63] Continuation-in-part of Ser. No. 946,056, Sep. 15, 1992, Pat. No. 5,480,969.

[51] Int. Cl.$^6$ .............................. C07K 7/00; C07K 7/06; A61K 38/00
[52] U.S. Cl. .......................................... 530/328; 530/313
[58] Field of Search ........................... 530/328, 313; 514/15-16

[56] References Cited

U.S. PATENT DOCUMENTS

| | | | |
|---|---|---|---|
| 2,872,484 | 2/1959 | Lecher et al. | 260/564 |
| 4,431,635 | 2/1984 | Coy et al. | 424/177 |
| 4,444,759 | 4/1984 | Rivier et al. | 424/177 |
| 4,504,414 | 3/1985 | Folkers et al. | 260/112.5 LH |
| 4,530,920 | 7/1985 | Nestor et al. | 514/15 |
| 4,647,653 | 3/1987 | Coy | 530/313 |
| 4,652,550 | 3/1987 | Rivier et al. | 514/15 |
| 4,801,577 | 1/1989 | Nestor, Jr. et al. | 514/15 |
| 4,851,385 | 7/1989 | Roeske | 514/15 |
| 4,935,491 | 6/1990 | Folkers et al. | 530/313 |
| 5,140,009 | 8/1992 | Haviv et al. | 514/16 |
| 5,300,492 | 4/1994 | Haviv et al. | 514/15 |

FOREIGN PATENT DOCUMENTS

| | | |
|---|---|---|
| 0 081 877 | 6/1983 | European Pat. Off. . |
| 0 097 031 | 12/1983 | European Pat. Off. . |
| 0 143 573 | 6/1985 | European Pat. Off. . |
| 0 162 575 | 11/1985 | European Pat. Off. . |
| 0 175 506 | 3/1986 | European Pat. Off. . |
| 0 197 798 | 10/1986 | European Pat. Off. . |
| 0 199 302 | 10/1986 | European Pat. Off. . |
| 0 225 746 | 6/1987 | European Pat. Off. . |
| 0 277 829 | 8/1988 | European Pat. Off. . |
| 0 328 090 | 8/1989 | European Pat. Off. . |

OTHER PUBLICATIONS

Karten, et al., "In Vitro Histamine Release with LHRH Analogs," *LHRH and Its Analogs; Contraceptive and Therapeutic Applications*, Part 2, eds. Vickery et al., pp. 179–190, 1987, published in England.

Humphries et al., "Inhibitory Analogues of the Luteinizing Hormone–Releasing Hormone Having D–Aromatic Residues in Positions 2 and 6 and Variation in Position 3," *Journal of Medicinal Chemistry*, 21(1):120–123, 1978, published in USA.

Janecka et al., "Design, Synthesis and Bioassays of Analogs of Argtide by Criteria of Potency and Safety," *Medicinal Chemistry Research*, 1:306–311, 1991, published in USA.

Ljungqvist et al., "Design, Synthesis and Biological Evaluation of Antagonists of LHRH by Criteria of Potency, Safety and Solubility," *Z. Naturforsch*, 46b:1231–1236, 1991, published in Europe.

Janecka et al., "Superiority of an Antagonist of the Luteinizing Hormone Releasing Hormone with Emphasis on Arginine in Position 8, Named Argtide," *Biochemical and Biophysical Research Communications*, 180(1):374–379, 1991, published in USA.

Amoss et al., "Purification, Amino Acid Composition and N–Terminus of the Hypothalamic Luteinizing Hormone Releasing Factor (LRF) of Ovine Origin," *Biochemical and Biophysical Research Communications*, 44(1):205–210, 1971, published in USA.

Bajusz et al., "New Antagonists of LHRH," *Int. J. Peptide Protein Res.*, 32:425–435, 1988, published in Europe.

Bajusz et al., "Highly Potent Antagonists of Luteinizing Hormone–Releasing Hormone Free of Edematogenic Effects," *Proc. Natl. Acad. Sci. USA*, 85:1637–1641, 1988, published in USA.

Dutta, Anand S., "Luteinizing Hormone–Releasing Hormone (LHRH) Antagonists," *Drugs of the Future*, 13(8):761–787, 1988, published in Europe.

Edelstein et al., "Single Dose Long–Term Suppression of Testosterone Secretion by a Gonadotropin–Releasing Hormone Antagonist (Antide) in Male Monkeys," *Contraception*, 42(2):209–215, 1990, published in USA.

Folkers et al., "Antagonists of the Luteinizing Hormone Releasing Hormone (LHRH) with Emphasis on the TRP$^7$ of the Salmon and Chicken II LHRH's," *Biochemical and Biophysical Research Communications*, 123(3):1221–1226, 1984, published in USA.

Folkers et al., "Increased Potency of Antagonists of the Luteinizing Hormone Releasing Hormone Which Have D–3–Pal in Position 6," *Biochemical and Biophysical Research Communications*, 137(2):709–715, 1986, published in USA.

Freidinger et al., "Bioactive Conformation of Luteinizing Hormone–Releasing Hormone: Evidence from a Conformationally Constrained Analog," *Science*, 210:656–658, 1980, published in USA.

Freidinger et al., "Protected Lactam–Bridged Dipeptides for Use as Conformational Constraints in Peptides," *J. Org. Chem.*, 47:104–109, 1982, published in USA.

Hahn et al., "Reproductive/Endocrine and Anaphylactoid Peptides of an LHRH–Antagonist, ORF 18260 [Ac–DNAL$^1$ (2), 4FDPhe$^2$, D–Trp$^3$, D–Arg$^6$]–GnRH," *Life Sciences*, 37:505–514, 1985 published in USA.

(List continued on next page.)

Primary Examiner—Cecilia J. Tsang
Assistant Examiner—Jennifer Harle
Attorney, Agent, or Firm—Arnold, White & Durkee

[57] ABSTRACT

LHRH analogs and congeners with high water solubility have been synthesized. These new analogs had 0%–100% antiovulatory activity at a 0.5 µg dosage and 0%–80% at 0.25 µg. The ED$_{50}$ for histamine release was 30.5 µg/ml–>300 µg/ml.

15 Claims, No Drawings

OTHER PUBLICATIONS

Humphries et al., "Presence of Proline in Position 3 for Potent Inhibition of the Activity of the Luteinizing Hormone Releasing Hormone and of Ovulation," *Biochemical and Biophysical Research Communications*, 72(3):939–944, 1976, published in USA.

Karten and Rivier, "Gonadotropin–Releasing Hormone Analog Design. Structure–Function Studies Toward the Development of Agonists and Antagonists: Rationale and Perspective," *Endocrine Reviews*, 7(1):44–66, 1986, published in USA.

Leal et al., "Prolonged Duration of Gonadotropin Inhibition by a Third Generation GNRH Antagonist," *Journal of Clinical Endocrinology and Metabolism*, 67(6):1325–1327, 1988, published in USA.

Leal et al., "Probing Studies on Multiple Dose Effects of Antide (NAL–LYS) GNRH Antagonist in Ovariectomized Monkeys," *Contraception*, 40(5):623–633, 1989, published in USA.

Lee et al., "Comparative Studies on the Hypotensive Effect of LHRH Antagonists in Anesthetized Rats," *Life Sciences*, 45:697–702, 1989, published in USA.

Ljungqvist and Folkers, "The Reaction of Pyridinecarboxylic Acids with Dicyclohexylcarbodiimide and p–Nitrophenol," *Acta Chemica Scandinavica*, B42:408–410, 1988, published in Europe.

Ljungqvist et al., "Design, Synthesis and Bioassays of Antagonists of LHRH Which Have High Antiovulatory Activity and Release Negligible Histamine," *Biochemical and Biophysical Research Communications*, 148(2):849–856, 1987, published in USA.

Ljungqvist et al., "Antide and Related Antagonists of Luteinizing Hormone Release with Long Action and Oral Activity," *Proc. Natl. Acad. Sci. USA*, 85:8236–8240, 1988, published in USA.

Ljungqvist et al., "Antagonists of LHRH Superior to Antide; Effective Sequence/Activity Relationships," *Tetrahedron*, 46(9):3297–3304, 1990, published in Europe.

Morgan et al., "Antagonistic Analogs of Luteinizing Hormone–Releasing Hormone Are Mast Cell Secretagogues," *Int. Archs. Allergy appl. Immun.*, 80:70–75, 1986, published in Europe.

Moroder et al., "Di–tert.–butyldicarbonat–ein vorteilhaftes Reagenz zur Einführung der tert.–Butyloxycarbonyl–Schutzgruppe," *Hoppe–Seyler's Z. Physiol. Chem.*, Bd. 357:S. 1651–1653, 1976, published in Europe.

Phillips et al., "Evaluation of the Anaphylactoid Activity of a New LHRH Antagonist," *Life Sciences*, 43:883–888, 1988, published in USA.

Rao et al., "Synthesis of 3–(3–pyridyl)– and 3–(3–benzo[b] thienyl)–D–alanine," *Int. J. Peptide Protein Res.*, 29:118–125, 1987, published in Europe.

Rivier et al., "New Effective Gonadotropin Releasing Hormone Antagonists with Minimal Potency for Histamine Release in Vitro," *J. Med. Chem.*, 29:1846–1851, 1986, published in USA.

Schally et al., "Gonadotropin–Releasing Hormone: One Polypeptide Regulates Secretion of Luteinizing and Follicle–Stimulating Hormones," *Science*, 173:1036–1038, 1971, published in USA.

Schmidt et al., "[Ac–D–NAL(2)[1], 4FD–Phe[2], D–Trp[3], D–Arg–[6]]–LHRH, A Potent Antagonist of LHRH, Produces Transient Edema and Behavioral Changes in Rats," *Contraception*, 29(3):283–289, 1984, published in USA.

Sundaram et al., "Antagonists of Luteinizing Hormone Releasing Hormone Bind to Rat Mast Cells and Induce Histamine Release," *Agents and Actions*, 25(3/4):307–313, 1988, published in Europe.

Tjoeng et al., "Vier Synthesewege zu (2–Pyrimidinylamino)–n–alkansäuren," *Chem. Ber.*, 108:862–874, 1975, published in Europe.

Benoiton, Leo, "Amino Acids and Peptides," *Canadian Journal of Chemistry*, 42:2043–2047, 1964, published in Canada.

Prasad et al., "Structure–Activity Relationships in Luteinizing Hormone–Releasing Hormone," *Journal of Medicinal Chemistry*, 19(4):492–495, 1976, published in USA.

Fife and Przystas, "Divalent Metal Ion Catalysts in the Hydrolysis of Esters of Picolinic Acid. Metal Ion Promoted Hydroxide Ion and Water Catalyzed Reactions," *J. Am. Chem. Soc.*, 107:1041–1047, 1985, published in USA.

Bernardi et al., "An Experimental Approach to Long–Lasting Hypotensive Eledoisin–Like Peptides," *J. Pharm. Pharmac.*, 19:95–101, 1967, published in Europe.

Peterman and Fauchère, "Synthesis of β–Pyrazinyl–L–Alanine (Paa)[1]) and of Peptide Derivatives," *Helvetica Chimica Acta*, 66(5):1513–1518, published in Europe.

Folkers et al., "Activities of Antagonists of the Luteinizing Hormone Releasing Hormone with Emphasis on Positions 1, 5 and 6 and on Positions 1, 2 and 3," *Z. Naturforsch, B: Chem. Sci.*, 42(1):101–106, 1987, published in Europe.

Hocart et al., "Effect of Reductive Alkylation of Lysine in Positions 6 and/or 8 on the Histamine–Releasing Activity of Luteinizing Hormone–Releasing Hormone Antagonists," *J. Med. Chem.*, 30(10):1910–1914, 1987, published in USA.

Hocart et al., "Effect of Reductive Alkylation of D–Lysine in Position 6 on the Histamine–Releasing Activity of Luteinizing Hormone–Releasing Hormone Antagonists," *J. Med. Chem.*, 30:739–743, 1987, published in USA.

Roeske and Chaturvedi, "Substitution of Arg[5] for Tyr[5] in GNRH Antagonists," *Peptides: Structure and Function*, Proceedings of the 9th American Pep. Sym., C.M. Deber, V.J. Hruby, K.D. Kopple (Editors), Pierce Chem. Co., Rockford, IL, pp. 561–564, Feb. 13, 1986, published in USA.

Leal et al., "Persistent Suppression of Gonadotropin Secretion by a Single Dose of 3rd Generation GnRH Antagonists in Primates," Abstract No. 882, name, date and place of publication unknown.

Channabasavaiah and Stewart, "New Analogs of Luliberin Which Inhibit Ovulation in the Rat," *Biochemical and Biophysical Research Communications*, 86(4):1266–1273, 1979, published in USA.

Channabasavaiah et al., "New Potent Agonist and Antagonist Analogs of Luteinizing Hormone Releasing Hormone," Peptides: Structure and Biological Function, Proceedings of the 6th/ American Peptides Symposium, Washington, D.C. pp. 803–806 (1979).

Nikolics and Spona, "In Vitro LH Release and cAMP Accumulation Induced by Synthetic GnRH Derivatives," *Peptides*, 5:1001–1006, 1984, published in USA.

Rivier et al., "GnRH Antagonists: N–Alkylation of Primary Amino Functions Generate New Potent Analogs," *Coll. Soc. Fr. Etudes Fertil.*, 26:25–31, 1988, published in Europe.

Lunenfeld et al., Eds., "The Rationale and Practice of GnRH Therapy," *The Current Status of GnRH Analogues*, Parthenon Pub. Group, Park Ridge, N.J., pp. 13–17, 1991, published in USA.

Nekola et al., "Antagonists of Luteinizing Hormone Releasing Hormone (LHRH): Potent Releasers of Histamine in Rats," *Clinical Research*, 32(5):865A, 1984, published in USA.

Hook et al., "Histamine Release by Structural Analogs of LHRH," *FASEB*, 44:1323, Abstract No. 5336, 1985, published in USA.

Miller et al., "Transdermal Iontophoresis of Gonadotropin Releasing Hormone (LHRH) and Two Analogues," *Journal of Pharmaceutical Sciences*, 79(6):490–493, 1990, published in USA.

Danforth et al., "Extended Presence of Antide (Nal–Lys GnRH Antagonist) in Circulation: Prolonged Duration of Gonadotropin Inhibition May Derive from Antide Binding to Serum Proteins," *Journal of Clinical Endocrinology and Metabolism*, 70(2):554–556, 1990, published in USA.

Horvath et al., "Synthesis and Biological Activity of LH–RH Antagonists Modified in Position 1," *Peptides*, 3:969–971, 1982, published in USA.

Folkers et al., "Advances on Chemical Structures of Effective Antagonists of the Luteinizing Hormone Releasing Hormone," *Med. Chem. Res.*, 1:235–239, 1991, published in USA.

Janecka et al., "Antagonists of the Luteinizing Hormone Releasing Hormone with Substitutions in Position 8," *Med. Chem. Res.*, 1:376–381, 1992, published in USA.

Gordon et al., "Minimal Effective Daily Dose of the GNRH Antagonist Antide Required to Achieve and Sustain Therapeutic Suppression of Estrogen Concentrations in Cynomolgue Monkeys," 73rd Annual Meeting of the American Endocrine Society, Abstract No. 1212, Jun. 19–22, 1991, published in USA.

Didolkar et al., "Effects of [derivatized] –LHRH (Nal–Lys) in Male Rats," 73rd Annual Meeting of the American Endocrine Society, Abstract No. 1704, Jun. 19–22, 1991, published in USA.

Aubert et al., "Long Lasting Inhibition of Gonadotropin Secretion by the GnRH Antagonist Antide: Evidence that Sustained GnRH Receptor Occupancy is Critical," 73rd Annual Meeting of the American Endocrine Society, Abstract No. 1688, Jun. 19–22, 1991, published in USA.

Joule et al., "Diazines: General Discussion and a Comparison with Pyridines and s–Triazine," *Heterocyclic Chemistry*, Chapter 9, pp. 123–125, Van Nostraad–Reinhold (London) 1972, published in Europe.

Roeske et al., "LHRH Antagonists with Low Histamine Releasing Activity," in *LHRH and its Analogs*, pp. 17–24, Vickery and Nestor, eds., MTP Press, Lancaster, UK (1987), published in Europe.

Rivier et al., "LHRH Analogs as Antiovulatory Agents," in *LHRH and its Analogs*, pp. 11–12, Vickery and Nestor, eds., MTP Press, Lancaster, UK (1987), published in Europe.

ANTAGONISTS OF LHRH

This is a continuation-in-part of application Ser. No. 07/946,056 filed Sep. 15, 1992 now U.S. Pat. No. 5,480,969 which is incorporated by reference herein.

This invention was made with government support under contract no. N01-HD-1-3101 awarded by the National Institutes of Health. The government, therefore, has certain rights in the invention.

BACKGROUND OF THE INVENTION

Many potent analogs of LHRH (the luteinizing hormone releasing hormone, pGlu$^1$, His$^2$, Trp$^3$, Ser$^4$, Tyr$^5$, Gly$^6$, Leu$^7$, Arg$^8$, Pro$^9$, Gly$^{10}$- NH$_2$) have structural features which cause release of histamine from mast cells (Karten et al., 1986). These features include a group of hydrophobic amino acids at the N-terminal and strongly basic residues in positions 6 and 8, notably D-Arg$^6$, Arg$^8$. A prime example of this class of analogs is (N-Ac-D-2-Nal$^1$, D-4F-Phe$^2$D-Trp$^3$, D-Arg$^6$)- LHRH (Schmidt et al.). Some analogs bind to rat peritoneal mast cells and membrane preparations and that the binding was related to the release of histamine (Sundaram et al.). For a recent review of LHRH analogs, see Janecka, et al. (1994).

Abbreviations for the unnatural amino acids mentioned herein are included in the following list:

| | |
|---|---|
| AABLys | N$^\epsilon$-(4-acetylaminobenzoyl)lysine |
| AALys | N$^\epsilon$-anisinoyl-lysine |
| AAPhe | 3-(4-acetylaminophenyl)lysine |
| Abu | 2-aminobutyric acid |
| ACLys | N$^\epsilon$-(6-aminocaproyl)lysine |
| ACyh | 1-aminocyclohexanecarboxylic acid |
| ACyp | 1-aminocyclopentanecarboxylic acid |
| Aile | alloisoleucine |
| Ala | alanine |
| AnGlu | 4-(4-methoxy-phenylcarbamoyl)-2-aminobutyric acid |
| 2ANic | 2-aminonicotinic acid |
| 6ANic | 6-aminonicotinic acid |
| APic | 6-aminopicolinic acid |
| APh | 4-aminobenzoic acid |
| APhe | 4-aminophenylalanine |
| APz | 3-amino-2-pyrazinecarboxylic acid |
| Aze | azetidine-2-carboxylic acid |
| Bim | 5-benzimidazolecarboxylic acid |
| BzLys | N$^\epsilon$-benzoyllysine |
| Cit | citrulline |
| Cl$_2$Phe | 3-(3,4-dichlorophenyl)alanine |
| Cpa | 3-(4-chlorophenyl)alanine |
| cPzACAla | cis-3-(4-pyrazinylcarbonylaminocyclohexyl)alanine |
| cPmACAla | cis-3-(4-(4-pyrimidylcarbonyl)aminocyclohexyl)alanine |
| Dbf | 3-(2-dibenzofuranyl)alanine |
| DMGLys | N$^\epsilon$-(N,N-dimethylglycyl)lysine |
| Dpo | N$^\epsilon$-(4,6-dimethyl-1-pyrimidyl)-ornithine |
| F$_2$Ala | 3,3-difluoroalanine |
| hNal | 4-(2-naphthyl)-2-aminobutyric acid |
| HOBLys | N$^\epsilon$-=(4-hydroxybenzoyl)lysine |
| hpClPhe | 4-(4-chlorophenyl)-2-amino-butyric acid |
| Hse | homoserine (2-amino-4-hydroxybutanoic acid) |
| ICapLys | N$^\epsilon$-(6-isopropylaminocaproyl)lysine |
| ILys | N$^\epsilon$-isopropyllysine |
| Ind | indoline-2-carboxylic acid |
| INicLys | N$^\epsilon$-isonicotincyllysine |
| IOrn | N$^\delta$-isopropylornithine |
| Me$_3$Arg | N$^G$,N$^G$,N$^G$-trimethylarginine |
| Me$_2$Lys | N$^\epsilon$, N$^\epsilon$-dimethyllysine |
| MNal | 3-((6-methyl)2-naphtyl)alanine |
| MNicLys | N$^\epsilon$-(6-methylpicolinoyl)lysine |
| MOB | 4-methoxybenzoyl |
| MpClPhe | N-methyl-3-(4-chlorophenyl)lysine |
| MPZGlu | glutamic acid, γ-4-methylpiperazine |
| NAcDNal | N-acetyl-3-12-naphthyl)alanine |
| NacDQal | N-acetyl-3-(3-quinolyl)alanine |
| Nal | 3-(2-naphthyl)alanine |
| Nap | 2-naphthoic acid |
| NapDThr | N-naphthoyl-D-threonine |
| NicLys | N$^\epsilon$-nicotinoyllysine |
| NO$_2$B | 4-nitrobenzoyl |
| NO$_2$Phe | 3-(4-nitrophenyl)alanine |
| oClPhe | 3-(2-chlorophenyl)alanine |
| Opt | O-phenyl-tyrosine |
| Orn | ornithine |
| Pal | 3-(3-pyridyl)alanine |
| 21Pal | 3-(2-pyridyl)alanine |
| 2PALys | N$^\epsilon$-(3-pyridylacetyl)lysine |
| pCapLys | N$^\epsilon$-(5-picolinoylaminocaproyl)lysine |
| pClPhe | 3-(4-chlorophenyl)alanine |
| pFPhe | 3-(4-fluorophenyl)-alanine |
| Pic | picolinic acid |
| PicLys | N$^\epsilon$-picolinoyllysine |
| PicSar | N-picolinoylsarcosinyl |
| Pip | piperidine-2-carboxylic acid |
| PmcLys | N$^\epsilon$--(4-pyrimidylcarbonyl)lysine |
| Ptf | 3-(4-trifluoromethyl) phenylalanine |
| Pz | pyrazinecarboxylic acid |
| PzAla | 3-pyrazinylalanine |
| PzAPhe | 3-(4-pyrazinylcarbonylaminophenyl)alanine |
| Qal | 3-(3-quinolyl)alanine |
| Qnd-Lys | N$^\epsilon$-quinaldoyllysine |
| Qui | 3-quinolinecarboxylic acid |
| Qux | 2-quinoxalinecarboxylic acid |
| Tic | 1,2,3,4-tetrahydroisoquinoline-3-carboxylic acid |
| TinGly | 2-thienylglycine |
| tNACAla | trans-3-(4-nicotinoylaminocyclohexyl)-alanine |
| tPACAla | trans-3-(4-picolinoylaminocyclohexyl)alanine |

SUMMARY OF THE INVENTION

LHRH analogs having the following formulas have been prepared and tested.

(NAcDQal$^1$, DPtf$^2$, DPal$^3$, cisPzACAla$^5$, DPicLys$^6$, DAla$^{10}$)LHRH (NAcDNal$^1$, DpClPhe$^2$, DPal$^3$, cisPzACAla$^5$, DNicLys$^6$, ILys$^8$, DAla$^{10}$)LHRH (NAcDNal$^1$, DpClPhe$^2$, DPal$^3$, Thr$^4$, PicLys$^5$, DPicLys$^6$, ILys$^8$, DAla$^{10}$)LHRH (NAcDNal$^1$, DpClPhe$^2$, DPal$^3$, PicLys$^5$, DPicLys$^6$, Thr$^7$, ILys$^8$, DAla$^{10}$)LHRH (NAcDThr$^1$, DpClPhe$^2$, DPal$^3$, PicLys$^5$, DPicLys$^6$, ILys$^8$, DAla$^{10}$)LHRH (NAcDNal$^1$, DpClPhe$^2$, DPal$^3$, NicLys$^5$, DNicLys$^6$, Thr$^7$, ILys$^8$,DAla$^{10}$)LHRH (NAcDNal$^1$, DpClPhe$^2$, DPal$^3$, Thr$^4$NicLys$^5$, DNicLys$^6$, Thr$^7$, ILys$^8$, DAla$^{10}$)LHRH (NAcDNal$^1$, DpClPhe$^2$, DPal$^3$, PicLys$^5$, D(PicSar) ILys$^6$, ILys$^8$, DAla$^{10}$)LHRH (NAcDNal$^1$, DpClPhe$^2$, DPal$^3$, D(PicSar)Lys$^6$, ILys$^8$, DAla$^{10}$)LHRH (NAcDNal$^1$, DpClPhe$^2$, DPal$^3$, PicLys$^5$, D(6ANic) Lys$^6$, ILys$^8$, DAla$^{10}$)LHRH (NAcDNal$^1$, DpClPhe$^2$, DPal$^3$, PicLys$^5$, D(6ANic) Orn$^6$, ILys$^8$, DAla$^{10}$)LHRH (NAcDQal$^1$, DCpa$^2$, DPal$^3$, cisPzACAla$^5$, DPicLys$^6$, NLeu$^7$, ILys$^8$, DAla$^{10}$)LHRH (NAcDNal$^1$, DCpa$^2$, DPal$^3$, DPicLys$^5$, DAPhe(PicSar)$^6$, ILys$^8$, DAla$^{10}$)LHRH (NAcDQal$^1$, DCpa$^2$, DPal$^3$, PicLys$^5$, DPal$^6$, ILys$^8$, DAla$^{10}$)LHRH (NAcDNal[1], DCpa[2], DPal[3], PicLys[5], DOrn (ACyp)[6], ILys[8], DAla[10])LHRH

DESCRIPTION OF THE PREFERRED EMBODIMENTS

LHRH analogs and congeners with high water solubility have been synthesized. These new analogs had 0%–100% antiovulatory activity at a 0.5 μg dosage and 0%–80% at 0.25 μg. The $ED_{50}$ for histamine release was 30.5 μg/ml–>300 μg/ml.

The compounds of the present invention are water soluble and some of them, as listed below, are also soluble in physiological salt solution without gelling. The preferred analogs show favorable potency and histamine values. These are important for clinical use and are not easily accomplished.

An important final point is that many LHRH analogs of the present invention do not contain the PzACAla substitution and still have favorable potency, histamine releasing effects and water solubility as well as solubility in physiological salt solution without gelling, except as listed below. The reason this is important is because the PzACAla is difficult to synthesize because of the stereochemical requirements, thus adding substantially to the expense of synthesis in large amounts. A concerted effort was made to eliminate the PzACAla for this very reason. As you know emphasis on the cost of drugs is a major issue these days.

Analogs 27316, 27345, 27234, 27459, and 27490 were soluble at 1 mg/ml in the physiological buffer solution PIPES-AC. Analog 27249 (1 mg/ml) and analog 27355 (0.3 mg/ml were slightly turbid. Analog 27274 gelled slightly at 1 mg/ml and analog 27163 gelled slightly at 1 mg/ml. For comparison, Antide gelled completely at 1 mg/ml while Lystide did not.

The following Examples are included to show the best mode of the present invention and not to limit the invention unless specifically claimed.

EXAMPLE 1

Design, Synthesis and Biological Evaluation of Analogs of LHRH by Criteria of Potency, Safety and Solubility Experimental Materials BOC-Ser(OBzl), BOC-Pro, BOC-Leu and BOC-D-Ala were obtained from Peninsula Laboratories, Belmont, CA. Abu was obtained from Sigma Chemical Company, St. Louis, Mo and it was converted to the BOC-derivative using standard procedures (Moroder et al.).

BOC-D-2-Nal, BOC-D-pClPhe, BOC-D- and L-3-Pal, BOC-ILys(Z) dicyclohexylamine salt, BOC-D- and L-NicLys and BOC-D-3-Qal were all provided by Dr. Narasimha Rao of the Southwest Foundation for Biomedical Research, San Antonio, Tex. BOC-D- and L-PzAla were synthesized by literature methods (Peterman et al.).

BOC-AOPP was kindly provided by Dr. R. M. Freidinger, Merck, Sharp & Dohme, West Point, Pa. (Freidinger et al., 1980 and 1982). α-BOC-cis-D- and L-4-aminocyclohexylalanine were provided by Dr. Narasimha Rao, and were converted to the corresponding BOC-cis-D-and L-PzACAla derivatives by acylation with the p-nitrophenylester (Folkers et al., 1990) of pyrazinecarboxylic acid from the Aldrich Chemical Company, Milwaukee, Wis., in DMF.

BOC-D- and L-PicLys were similarly prepared from α-BOC-D-and L-Lys and picolinic acid p nitrophenylester (Ljungqvist et al.) in DMF. α-BOC-D- and L-(DSer)Lys, protected at the D-Ser moiety by the Z group at the amino group and by the benzyl group at the hydroxyl function, were synthesized by acylation of BOC-D- and L-Lys in DMF by Z-D-Ser(OBzl)-ONp in the presence of 1-hydroxybenzotriazole. The BOC-D-(AcDSer)Lys, protected as the benzyl derivative at the D-Ser hydroxy, was similarly prepared by the reaction between Ac-D-Ser(OBzl) ONp and BOC-D-Lys.

All synthesized amino acids and intermediates were characterized by NMR and were homogenous on TLC.

The benzhydrylamine hydrochloride resin was purchased from Beckman Bioproducts, Palo Alto, Calif. The dicyclohexylcarbodiimide was from Aldrich and was distilled in vacuo before use. The dichloromethane was distilled from sodium carbonate. All other solvents and reagents were reagent grade.

Synthesis

The peptides were synthesized by the solid-phase method using a Beckman automated 990 peptide synthesizer. The protocol details used were essentially as described (Folkers et al., 1984). The peptide was cleaved from the resin with concomitant removal of all protecting groups by treatment with doubly distilled HF at 0° C. for 1 h in the presence of about 10% anisole in p-cresol. The HF was then evaporated, in vacuo, first by a water aspirator and then by pump vacuum overnight. The residue was then extracted 2–3 times with ether in order to remove non-peptidic material. The crude peptide was subsequently extracted with aqueous acetic acid and the extract was lyophilized.

Purification and Characterization

Purification was achieved by chromatography on $SiO_2$ (EM, 230–400 mesh) with the solvent system n-butanol:acetic acid:water 4:1:2 or 4:1:5 (upper phase) followed by gel filtration on Sephadex G 25 with 6% aqueous acetic acid as the eluant. An alternative purification method was gel filtration as above followed by chromatography on Sephadex LH 20 with the solvent system water:butanol:acetic acid:methanol 90:10:10:8.

The purity was checked by TLC, amino acid analysis and HPLC.

Amino acid analyses were carried out on a Beckman 118 CL amino acid analyzer after hydrolysis in constant boiling HCl for 24 h using standard procedures (Folkers et al., 1984). The unnatural amino acids were qualitatively determined with the exception of 3-Pal which was quantified.

The purity was further checked by HPLC using a Waters instrument with a 660 solvent programmer and a Vydac $C_{18}$ column. The flow rate was 1.5 ml/min and the absorbance was recorded at 210 nm. Different gradients of increasing concentration of acetonitrile in 0.01M $KH_2PO_4$, adjusted to pH 3 with $H_3PO_4$, were employed. All peptides were estimated to be 97–99% pure in this system (data not shown).

Biological assays

AOA in rats was determined as reported (Humphries et al.). The histamine release was assayed in rat mast cells as reported (Hook et al., Karten et al., 1987). The $ED_{50}$ value reported is the concentration in μg/ml that releases 50% of total releasable histamine. The biological data are in the following table. These are more completely explained in U.S. Pat. No. 4,935,491 that is incorporated, in pertinent part, by reference herein.

LHRH ANALOGS, STRUCTURE AND BIOLOGICAL ACTIVITY

| CPD # | DOSAGE μg | AOA % INHIB (#OVUL #RATS) | HISTAMINE μg/ml $ED_{50}$ | STRUCTURE* |
|---|---|---|---|---|
| 27163 | 0.25 | 100 (0/5) | 40 ± 0 | (NAcDQal$^1$, DPtf$^2$, DPal$^3$, cisPzACAla$^5$, DPucKts$^6$, DAla$^{10}$) LHRH |
|  | 0.125 | 22 (7/9) |  |  |
| 27234 | 0.5 | 100 (0/6) | 104 ± 4 | (NAcDNAl$^1$, DpClPhe$^2$, DPal$^3$, cisPzACAla$^5$, DNicLys$^6$, ILys$^8$, DAla$^{10}$) LHRH |
|  | 0.25 | 67 (2/6) |  |  |
| 27249 | 0.5 | 100 (0/5) | 95 ± 5 | (NAcDNal$^1$, DpClPhe$^2$, DPal$^3$, Thr$^4$, PicLys$^5$, DPicLys$^6$, ILys$^8$, DAla$^{10}$) LHRH |
|  | 0.25 | 17 (5/6) |  |  |
| 27274 | 0.5 | 100 (0/5) | 30.5 ± 2 | (NAcDNal$^1$, DpClPhe$^2$, DPal$^3$, PicLys$^5$, DPicLys$^6$, Thr$^7$, ILys$^8$, DAla$^{10}$) LHRH |
|  | 0.25 | 17 (5/6) |  |  |
| 27306 | 0.5 | 20% | 100 ± 0 | (NapDthr$^1$, DpClPhe$^2$, DPal$^3$, PicLys$^5$, DPicLys$^6$, ILys$^8$, DAla$^{10}$) LHRH |
| 27313 | 0.5 | 0 | 298 ± 3 | (NacDNAl$^1$, DpClPhe$^2$, DPal$^3$, NicLys$^5$, DNicLys$^6$, Thr$^7$, ILys$^8$, DAla$^{10}$) LHRH |
| 27315 | 0.5 | 0 | 100 ± 0 | (NAcDNal$^1$, DpClPhe$^2$, DPal$^3$, Thr$^4$, NicLys$^5$, DNicLys$^6$, Thr$^7$, ILys$^8$, DAla$^{10}$) LHRH |
| 27316 | 0.5 | 100 (0/5) | 34 ± 2 | (NacDNal$^1$, DpClPhe$^2$, DPal$^3$, PicyLys$^5$, D (PicSar) Lys$^6$, ILys$^8$, DAla$^{10}$) LHRH |
|  | 0.25 | 50 (5/10) |  |  |
| 27345 | 0.5 | 100 (0/10) | 31.5 ± 2 | (NAcDNAl$^1$, DpClPhe$^2$, DPal$^3$, D (PicSar) Lys$^6$, ILys$^8$, DAla$^{10}$) LHRH |
|  | 0.25 | 33 (4/6) |  |  |
| 27355 | 0.5 | 83 (1/6) | 96 ± 0 | (NAcDNal$^1$, DpClPhe$^2$, DPal$^3$, PicLys$^5$, D (6ANic) Lys$^6$, ILys$^8$, DAla$^{10}$) LHRH |
|  | 0.25 | 50 (3/6) |  |  |
| 27459 | 0.5 | 100 (0/6) | 100 ± 0 | (NAcDNal$^1$, DpClPhe$^2$, DPal$^3$, PicLys$^5$, D (6ANic) Orn$^6$, ILys$^8$, DAla$^{10}$) LHRH |
|  | 0.25 | 25 (3/4) |  |  |
| 27490 | 0.5 | 100 (0/5) | 200 ± 100 | (NacDQal$^1$, DCpa$^2$, DPal$^3$, cisPzACAla$^5$, DPicLys$^6$, NLeu$^7$, ILys$^8$, DAla$^{10}$) LHRH |
|  | 0.25 | 80 (2/10) |  |  |
| 27535 | 0.5 | 86% | 275 ± 25 | (NAcDNAl$^1$, DCpa$^2$, DPal$^3$, DPicLys$^5$, DAPhe (PicSar)$^6$, ILys$^8$, DAla$^{10}$) LHRH |
|  | 0.25 | 20% |  |  |
| 27542 | 0.5 | 100% | >300 | (NAcDQal$^1$, DCpa$^2$, DPal$^3$, PicLys$^5$, DPal$^6$, ILys$^8$, DAla$^{10}$) LHRH |
|  | 0.25 | 0% |  |  |
| 27629 | 0.5 | 100% | NA | (NAcDNal$^1$, DCpa$^2$, DPal$^3$, PicLys$^5$, DOrn (ACyp)$^6$, ILys$^8$, DAla$^{10}$) LHRH |
|  | 0.25 | 17% |  |  |

*Unspecified positions are from LHRH (pGlu$^1$, His$^2$, Trp$^3$, Ser$^4$, Tyr$^5$, Gly$^6$, Leu$^7$, Arg$^8$, Pro$^9$, Gly$^{10}$—NH$_2$)

The following citations are incorporated in pertinent part by reference herein for the reasons cited in the above text.

References

Folkers et al., (Jun. 19, 1990) U.S. Pat. No. 4,935,491.
Folkers et al., Biochem, Biophys. Res. Commun. 123, 1221 (1984).
Freidinger et al., Since 210, 656 (1980)
Freidinger et al., J. Org. Chem. 47 104 (1982).
Humphries et al., *Biochem. Biophys. Res. Comm.* (1976) 72, 939–944.
Humphries et al., (1987) *J. Med. Chem.* 21, 120–123.
Janecka et al. (1994) *Amino Acids* 6,111–130.
Karten et al., (1986) *Endocr. Rev.* 7: 44–66.
Karten et al., in: LHRH and its Analogs: Contraceptive and Therapeutic Applications II, pp. 179–190, MTP Press LTD, Lancaster, England (1987).
Ljungqvist et al., (1988) *Acta Chem. Scand.* 842: 408–410.
Ljungqvist et al., (1987) *Biochem. Biophys Res. Comm.* 148: 849–856.
Ljungqvist et al., Proc. Natl. Acad. Sci. USA 85, 8236 (1988).
Moroder et al., Hoppe-Seyler's Z. Physiol. Chem. 357, 1651(1976).
Peterman et al., Helv. Chim. Acta 66, 1513 (1983).
Rao et al., (1987) *Int. J. Peptide Protein Res.* 29: 118–125.
Schmidt et al., (1984) Contraception 29: 283–289.
Sundaram et al., Agents and Actions 25, 307 (1988).

What is claimed is:

1. An LHRH analog having the formula (NAcDQal$^1$, DPtf$^2$, DPAl$^3$, cisPzACAla$^5$, DPicLys$^6$, DAla$^{10}$)LHRH.

2. An LHRH analog having the formula
(NAcDNal$^1$, DpClPhe$^2$, DPal$^3$, cisPzACAla$^5$, DNicLys$^6$, ILys$^8$, DAla$^{10}$)LHRH.

3. An LHRH analog having the formula
(NAcDNal$^1$, DpClPhe$^2$, DPal$^3$, Thr$^4$, PicLys$^5$, DPicLys$^6$, ILys$^8$, DAla$^{10}$)LHRH.

4. An LHRH analog having the formula
(NAcDNal$^1$, DpClPhe$^2$, DPal$^3$, PicLys$^5$, DPicLys$^6$, Thr$^7$, ILys$^8$, DAla$^{10}$)LHRH.

5. An LHRH analog having the formula
(NapDThr$^1$, DpClPhe$^2$, DPal$^3$, PicLys$^5$, DPicLys$^6$, ILys$^8$, DAla$^{10}$)LHRH.

6. An LHRH analog having the formula
(NAcDNal$^1$, DpClPhe$^2$, DPal$^3$, NicLys$^5$, DNicLys$^6$, Thr$^7$, ILys$^8$, DAla$^{10}$)LHRH.

7. An LHRH analog having the formula
(NAcDNal$^1$, DpClPhe$^2$, DPal$^3$, Thr4NicLys$^5$, DNicLys$^6$, Thr$^7$, ILys$^8$, DAla$^{10}$)LHRH.

8. An LHRH analog having the formula
(NAcDNal$^1$, DpClPhe$^2$, DPal$^3$, PicLys$^5$, D(PicSar)Lys$^6$, ILys$^8$, DAla$^{10}$)LHRH.

9. An LHRH analog having the formula
(NAcDNal$^1$, DpClPhe$^2$, DPal$^3$, D(PicSar)Lys$^6$, ILys$^8$, DAla$^{10}$)LHRH.

10. An LHRH analog having the formula
(NAcDNal$^1$, DpClPhe$^2$, DPal$^3$, PicLys$^5$, D(6ANic) Lys$^6$, ILys$^8$, DAla$^{10}$)LHRH.

11. An LHRH analog having the formula
(NAcDNal$^1$, DpClPhe$^2$, DPal$^3$, PicLys$^5$, D(6ANic )Orn$^6$, ILys$^8$, DAla$^{10}$)LHRH.

12. An LHRH analog having the formula
(NAcDQal$^1$, DCpa$^2$, DPal$^3$, cisPzACAla$^5$, DPicLys$^6$, NLeu$^7$, ILys$^8$, DAla$^{10}$)LHRH.

13. An LHRH analog having the formula
(NAcDNal$^1$, DCpa$^2$, DPal$^3$, DPicLys$^5$, DAPhe(PicSar)$^6$, ILys$^8$, DAla$^{10}$)LHRH.

14. An LHRH analog having the formula
(NAcDQal$^1$, DCpa$^2$, DPal$^3$, PicLys$^5$, DPal$^6$, ILys$^8$, DAla$^{10}$)LHRH.

15. An LHRH analog having the formula
(NAcDNal$^1$, DCpa$^2$, DPal$^3$, PicLys$^5$, DOrn(ACyp)$^6$, ILys$^8$, DAla$^{10}$)LHRH.

* * * * *